(12) United States Patent  (10) Patent No.: US 6,668,398 B2
Lane  (45) Date of Patent: Dec. 30, 2003

(54) BED AIR BAG DETERRENT SYSTEM

(75) Inventor: Stephen S. Lane, Bethesda, MD (US)

(73) Assignee: Amron Corporation, McLean, VA (US)

( * ) Notice: Subject to any disclaimer, the term of this patent is extended or adjusted under 35 U.S.C. 154(b) by 0 days.

(21) Appl. No.: 09/826,808

(22) Filed: Apr. 6, 2001

(65) Prior Publication Data

US 2002/0144345 A1 Oct. 10, 2002

(51) Int. Cl.[7] ............................................... G08B 21/00
(52) U.S. Cl. ............................................... 5/424; 5/904
(58) Field of Search ........................ 5/424, 425, 426, 5/655.3, 904, 945

(56) References Cited

U.S. PATENT DOCUMENTS

| 5,052,065 A | | 10/1991 | West |
| 5,066,943 A | * | 11/1991 | Demirel et al. .......... 340/573.4 |
| 5,471,198 A | * | 11/1995 | Newham ................. 340/573.4 |
| 5,592,705 A | | 1/1997 | West |
| 5,611,096 A | | 3/1997 | Bartlett et al. |
| 5,636,862 A | | 6/1997 | Cheung et al. |
| 5,690,355 A | | 11/1997 | Kleinberg |
| 5,730,464 A | | 3/1998 | Hill |
| 5,765,867 A | | 6/1998 | French |
| 5,808,552 A | * | 9/1998 | Wiley et al. ............. 340/573.4 |
| 5,876,059 A | | 3/1999 | Kleinberg |

* cited by examiner

*Primary Examiner*—Heather Shackelford
*Assistant Examiner*—Fredrick Conley
(74) *Attorney, Agent, or Firm*—Arent Fox Kintner Plotkin & Kahn, PLLC

(57) ABSTRACT

A bed air bag deterrent apparatus for deterring a bed occupant from getting out of bed without assistance of a caregiver, including a deterrent device mounted on a bed frame and activated by a detection system to deter or delay the bed occupant from getting out of bed, a detection system having a detector for detecting when the bed occupant is attempting to get out of bed, and a control mechanism to for controlling the detection and deterrent systems. The deterrent device has an inflatable air bag mounted on the long side of a horizontally displaced rectangular support frame that is positioned on the horizontal surface of a bed frame. The detection system includes transmitters, sensors and pressure-sensitive bed occupancy pads for detecting the bed occupant. The control mechanism includes a bed occupancy monitor and audio system.

9 Claims, 6 Drawing Sheets

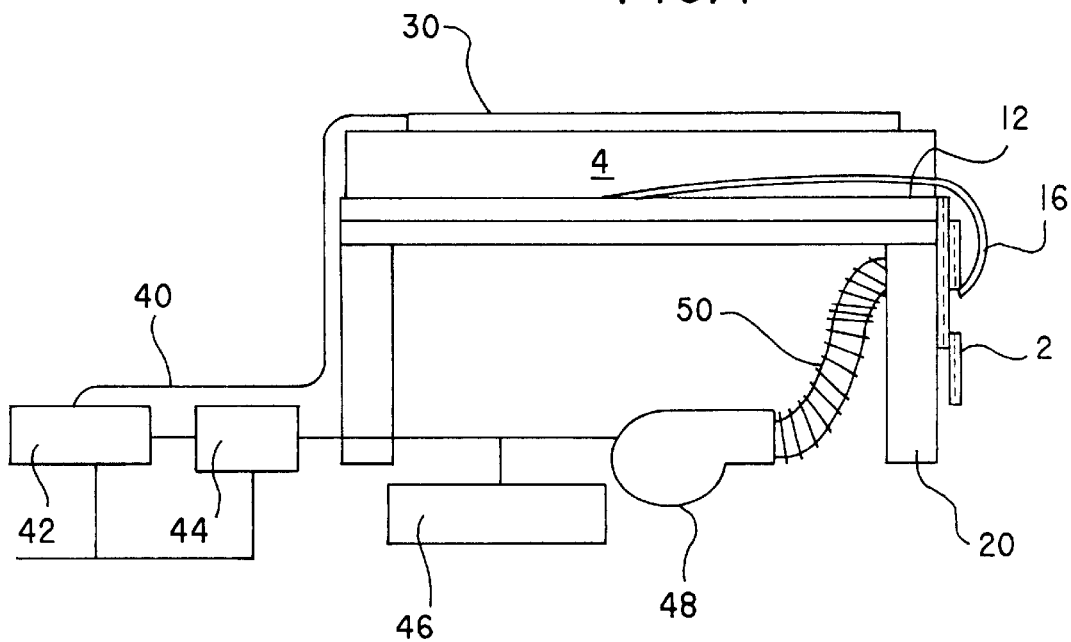
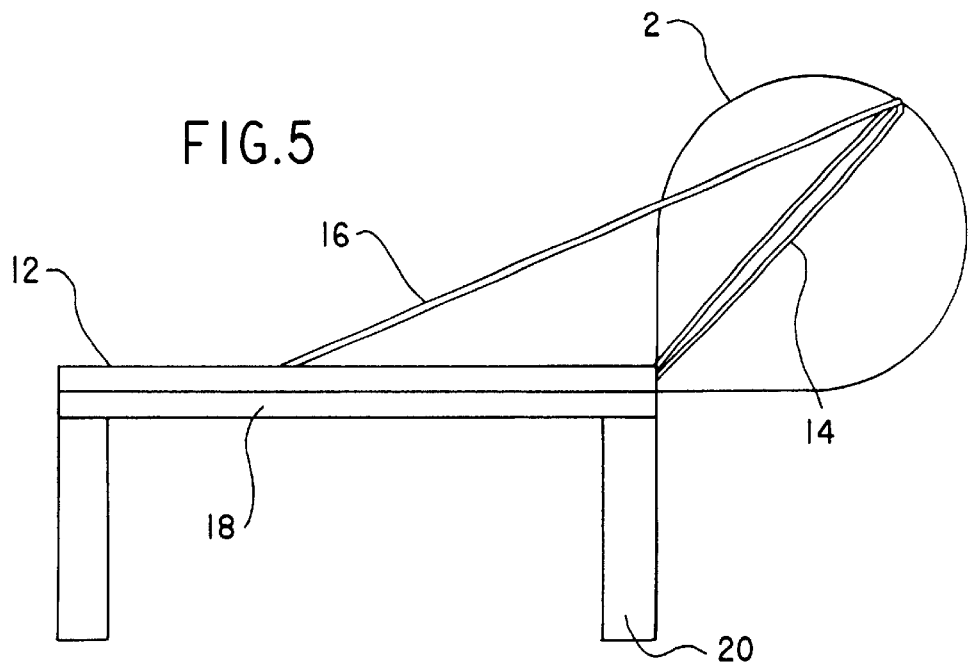

BED AIR BAG DETERRENT SYSTEM

FIELD OF THE INVENTION

The present invention relates generally to safety equipment, and in particular, to an inflatable air bag to deter a patient from getting out of bed and walking without the supervision or assistance of a caregiver.

BACKGROUND

It is well known that hospital patients such as the elderly or those with Alzheimer's disease are in danger when they attempt to walk or move unaided from a bed. But an initial problem arises when they attempt to leave their bed as they are either physically too weak, or too confused to negotiate a safe exit. As a result, upon their attempted exit, they may misstep, fall out of the bed and injure themselves. Not only do these falls sometimes result in serious injuries, but they may also result in fatalities. Statistics show that falls in older persons and their resulting emotional effects, such as depression, are the leading cause of unintentional death in people over 75 years of age.

Over the years, hospitals and nursing homes have used different forms of impediments to prevent patients from leaving their beds. Physical deterrents have been used to tie bed occupants to the bed. These deterrents, however, are degrading, threatening, and have a tendency to agitate patients, particularly if they are confused about their surroundings. Also, railings have been used for many years. Recent studies, however, have shown that not only do railings fail to prevent falls, but they may actually increase serious injuries to bed occupants who attempt to climb over the railings to get out of the bed. Hospital and nursing home patients should have some level of comfort, but prior deterring systems with these and other drawbacks have diminished the quality of life of patient hospitalization. Therefore, a need exists in hospitals, nursing homes and even hospice or home care arrangements, to provide patients with a non-threatening deterrent.

U.S. Pat. No. 5,592,705, to West, discloses an impact cushioning device that rests on a floor to cushion a patient who has fallen off of a bed. However this device does not become effective until the patient is already falling off of the bed so, it does not prevent the fall. The same is true of U.S. Pat. No. 5,052,065, also to West, that discloses a cushion to protect wheelchair or bed occupants from fall-related injuries. Since the cushion rests at a distance from its supporting structure, the occupant has some distance to travel before the fall is cushioned.

When a cushion rests on the floor, it is possible that the bed or wheelchair occupant may bounce off the cushion and still land on the floor. Also, the occupant may grab at the surroundings or nearby objects in an attempt to prevent an impending fall (from either the bed or wheelchair) even though there is a cushion on the floor, resulting in a muscle strain. Thus, neither one of these devices prevents the full range of injuries that could occur should a patient either attempt to break their own fall or fall off of the cushion.

SUMMARY OF THE INVENTION

It is the primary object of the present invention to provide a new and improved device to safeguard and deter patients who attempt to get out of their bed without the supervision or assistance of a caregiver. This device is particularly valuable for safeguarding patients in hospitals and nursing homes or where patients are under a hospice care-like arrangement.

It is another object of the present invention to provide a detection system to detect when an occupant is attempting to get out of bed.

It is another object of the present invention to provide a control mechanism to carry a signal to an audio system and an inflation device such as a fan for activating a deterrent device to deter or delay an occupant from getting out of bed.

It is another object of the present invention to provide a method of detecting and deterring a bed occupant from getting out of bed.

The present invention is directed to an apparatus to deter a bed occupant from getting out of a bed including a detection system, a deterrent device and a control mechanism. The detection system has a three-component detector for detecting when the bed occupant is attempting to get out of the bed. The deterrent device includes an air bag that is mounted on the frame of the bed that inflates to deter or delay the bed occupant from getting out of bed in response to a detection system signal. The control mechanism controls the detection system and deterrent device. The air bag is mounted on the long side of the bed and affixed to a support board or support frame on a bed frame. The air bag is inflated using a low-pressure inflation fan triggered by the control mechanism. When deployed, the air bag is maintained in a proper position by external tethers.

BRIEF DESCRIPTION OF THE DRAWINGS

FIG. 4 is an end view of a bed with the sensor system of the present invention;

FIG. 5 is an end view of the bed with a side view of the inflated air bag of the present invention;

DETAILED DESCRIPTION OF THE PREFERRED EMBODIMENT

Figure 1:
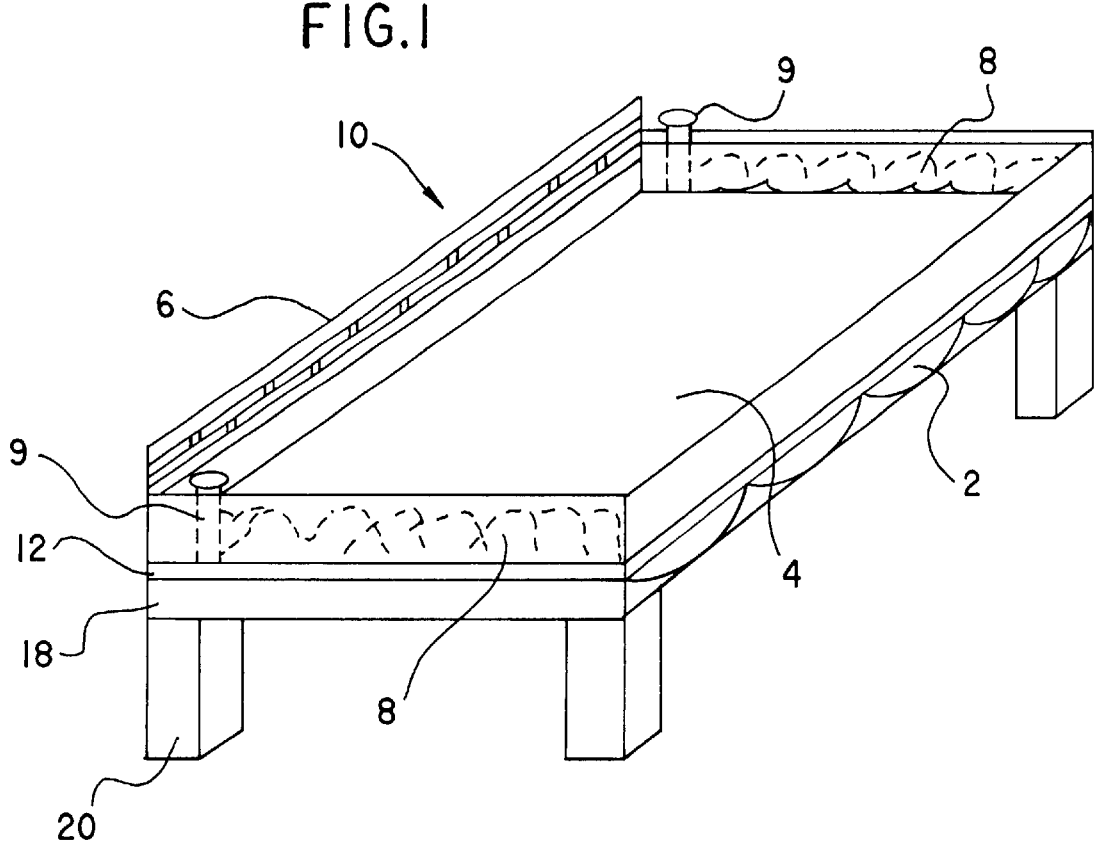
FIG. 1 is a perspective view of a bed with a deflated air bag of the present invention.

FIG. 1 illustrates a bed frame 10 including a horizontally disposed support platform 18 positioned between the bed frame 10 and a mattress 4 and four support members or legs 20 integrally connected to the four corners of the support platform 18. Alternatively, a support frame 12 and four support members or legs 20 integrally connected to the four corners of the frame 12 can be positioned between the bed frame 10 and a mattress 4. The support platform 18 can be constructed from plywood, Masonite, a light metal or any other suitable and economical material.

The support frame 12 is substantially flat and can be of any shape, but preferably is a rectangular-like frame of PVC pipe that substantially covers the bed frame 10. The support frame 12 is positioned on top of the bed frame 10. The mattress 4 rests upon the bed frame 10 inside the support frame 12, or on top of the support platform 18 depending on which is used.

Figure 2:
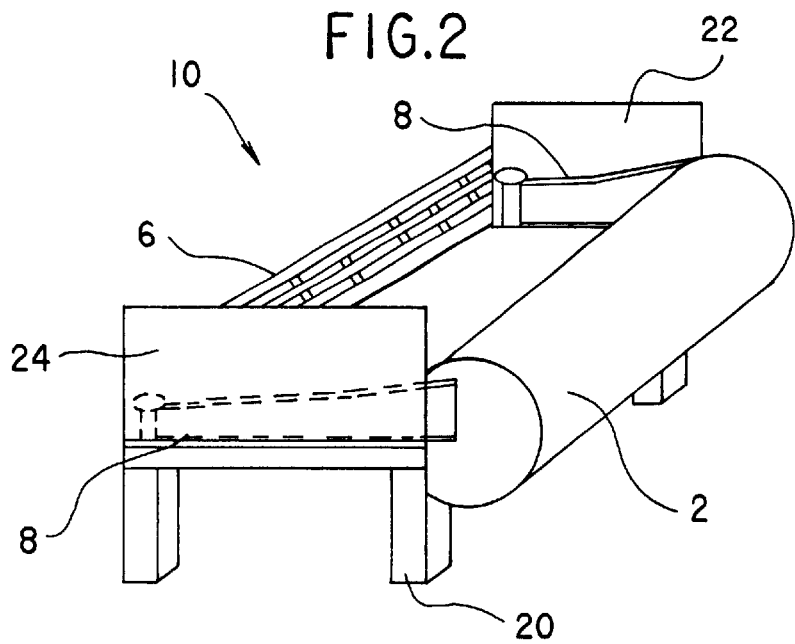
FIG. 2 is a perspective view of a bed with an inflated air bag of the present invention.
Figure 2A:
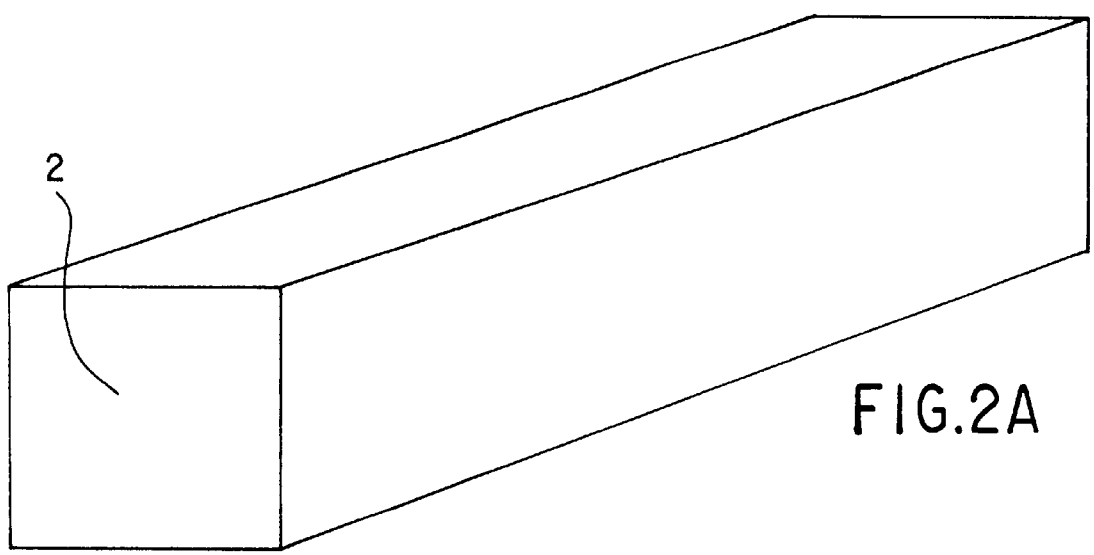
FIGS. 2A to 2C are perspective cross-sectional views of air bags of the present invention.
Figure 2B:
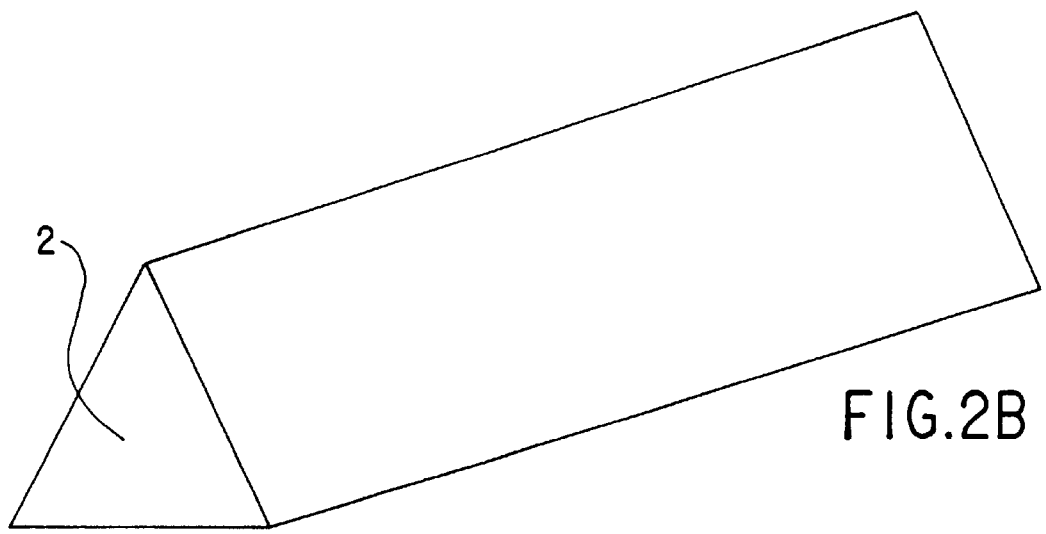
Figure 2C:
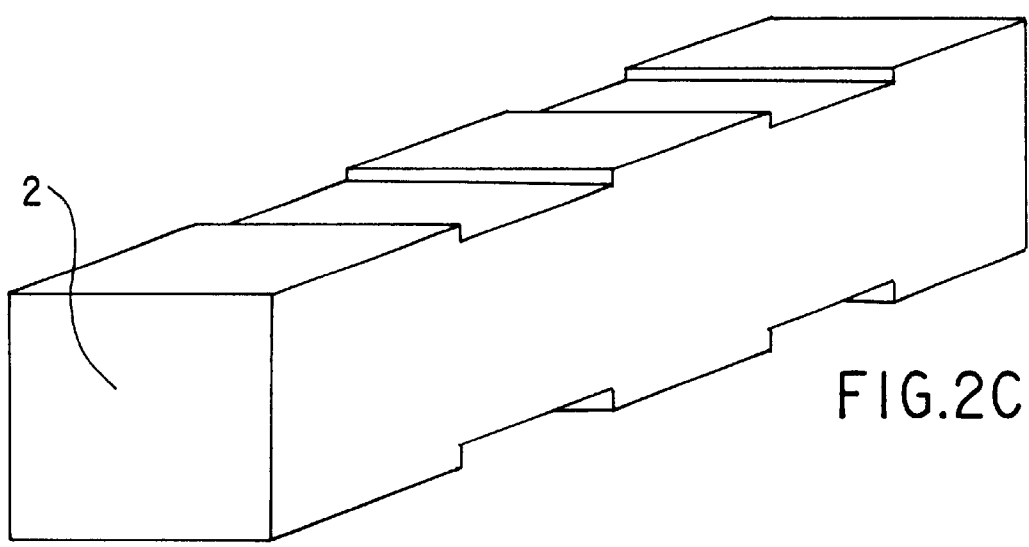

Referring to FIG. 2, the air bag 2 inflates upwardly and along the long side of the bed 10. As illustrated, the inflated air bag 2 can be cylindrical with a circular cross-section. However, the air bag 2 can be of any suitable cross-section such as, for example, rectangular, triangular and the like. See FIGS. 2A–2C. The bag should be long enough to close or almost close the end of the bed with either no gap or a very small gap. The diameter of the bag should be the minimum required for deterrence. The maximum size is preferably 2 feet in diameter. The critical feature of the air bag cross-section is that the size and shape of the air bag are sufficient to deter or delay a bed occupant from getting out of the bed without assistance or supervision from the caregiver. This is because the inflated air bag 2 deters or delays the bed occupant to provide a necessary amount of time for the caregiver to attend to the bed occupant attempting to get out of the bed or at least keep the occupant in the bed. The air bag in the preferred embodiment is made from ripstop nylon, i.e., parachute cloth. However, an air bag made from any suitable air bag material can be used.

Although illustrated as having an air bag on one side only, two air bags can be used, one on either side of the bed. As such, both bags may activate simultaneously or individually, depending on which side of the bed receives the signal of the bed occupants' attempted exit. However, when only one air bag 2 is used, a railing 6 can be used on the opposite side of the bed. With the railing 6 on the opposite side, the bed occupant will attempt to leave the bed via the open (i.e., deflated air bag) side. The deflated air bag 2 (FIGS. 1 and 4) is stored by a suitable retention device such as elastic bands on the side of the bed 10 opposite the railing 6. Inside the air bag, a coil 60 of wire keeps the bag material from entering and clogging the intake duct when the same duct is used to deflate the bag. The air bag 2 is unobtrusive when not being used (i.e., deflated). When not inflated, the air bag 2 does not interfere with the caregiver's duties around the bed or with a person leaving the bed with the aid of a caregiver. Thus, the deflated air bag 2 can be compactly stored next to the left, right or both sides of the bed substantially along the long side of the bed.

Figure 6:
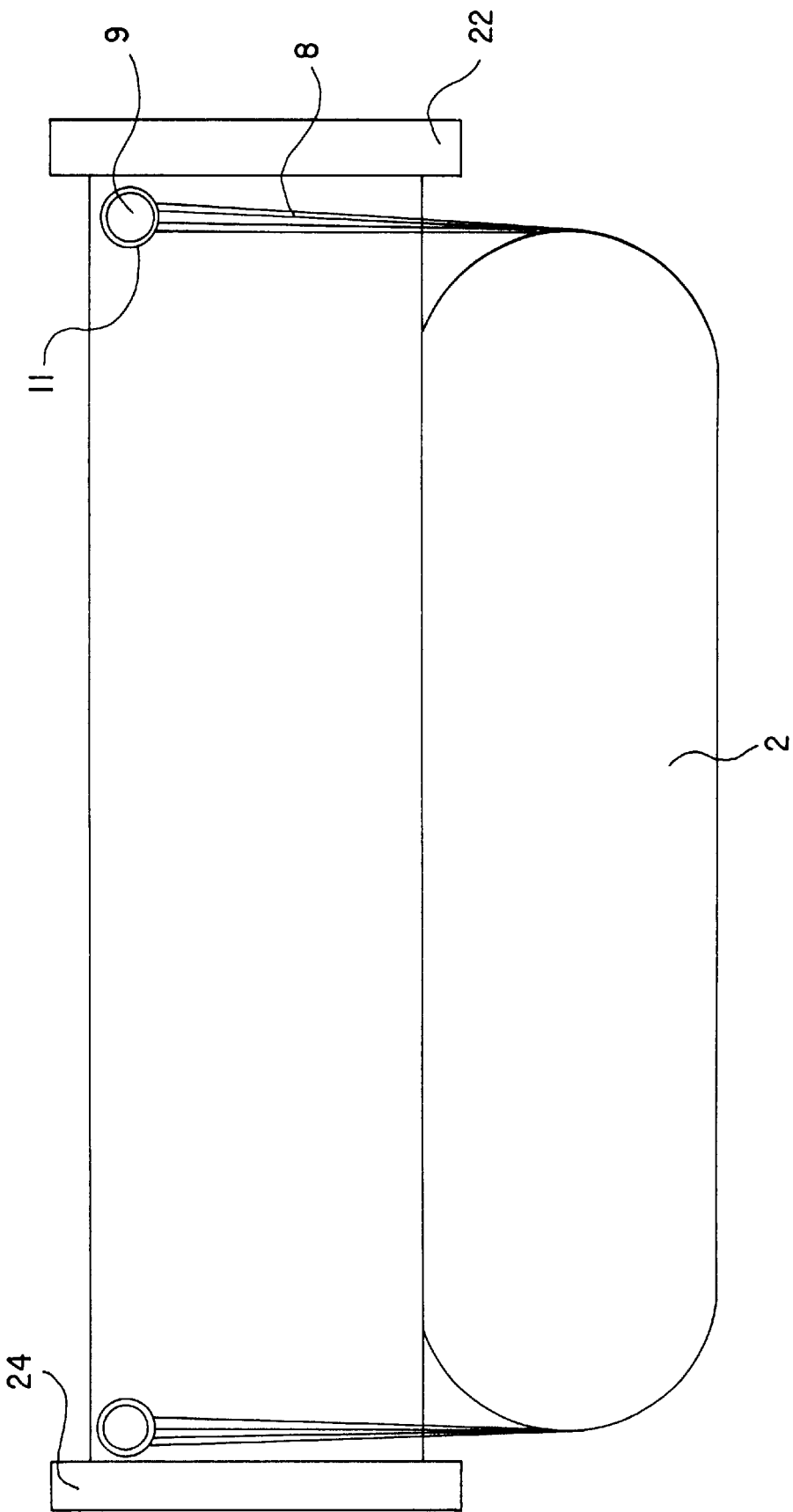
FIG. 6 is a top view of the bed with the inflated air bag of the present invention.

Support panels 8, extend from the ends of the air bag and are attached to the members or legs 20 on the opposite side of the bed from the bag and at the head and foot of the bed to close the gap between a headboard 22 of the bed and the air bag 2 as well as the gap between the footboard 24 of the bed and the air bag 2. See FIG. 6. The support panels also prevent the air bag from rotating down and away from the bed when the occupant presses on the air bag while in the bed. The support panels 8 are also ripstop nylon. The headboard 22 and footboard 24 can be of any convenient material such as plywood, Masonite or a light metal, and should be detachable so that the bed air bag deterrent apparatus can be stored when not in use.

Figure 3:
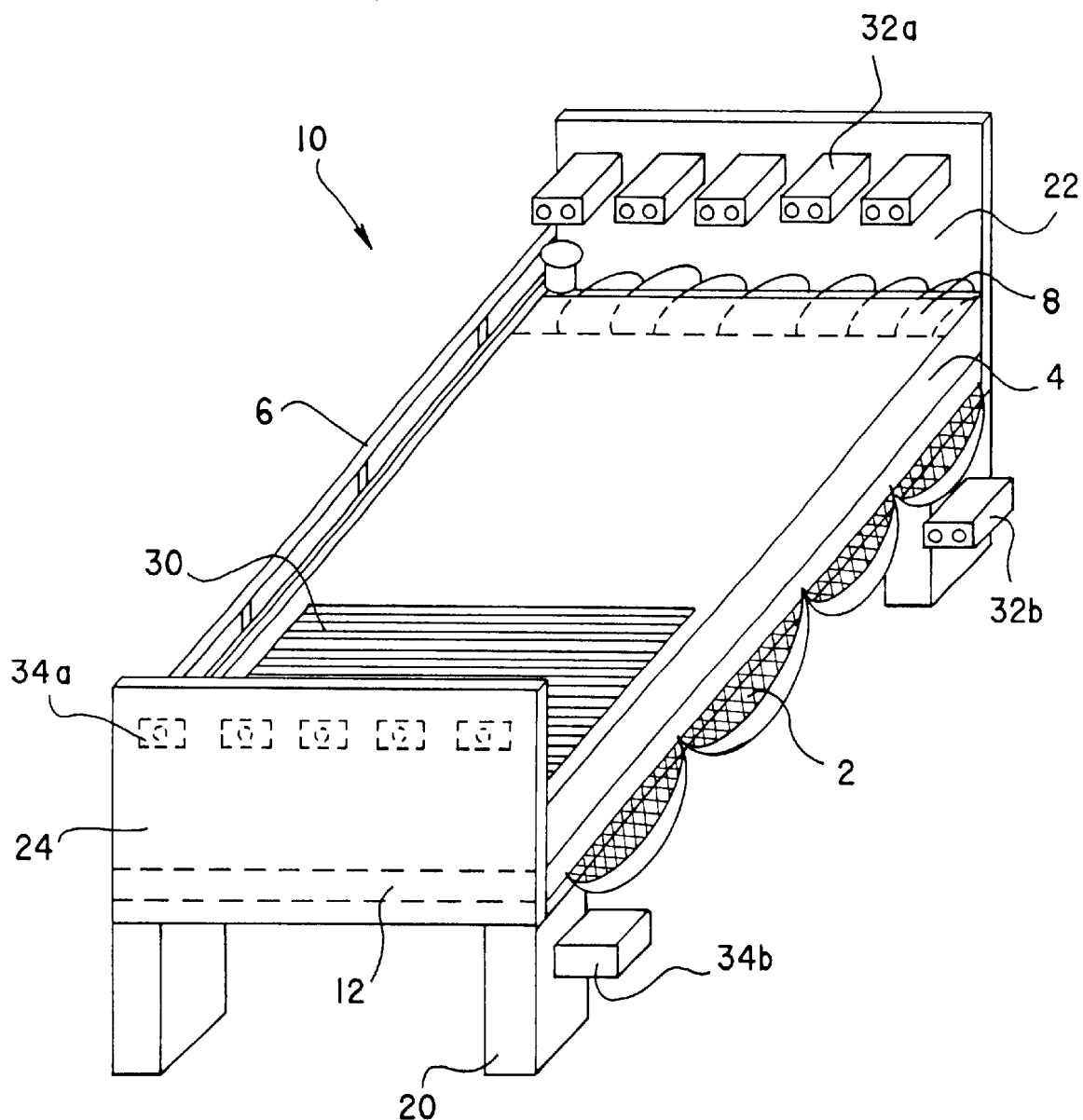
FIG. 3 is a perspective view of a bed with transmitters and reflectors/receivers of the present invention.

FIG. 3 illustrates the detection system to indicate when an occupant is attempting to leave the bed. The detection system is activated by a switch (not shown) located near the bed, for example, on a nightstand. The detection system has three components: pressure-sensitive pads 30, at least one set of transmitters 32a with sensors 34a (reflectors or receivers) above the bed, and at least one set of transmitters 32b with sensors 34b (reflectors or receivers) by the side of or below the bed. The sensors are positioned opposite a corresponding transmitter to receive the signal from the transmitter therefore, each transmitter 32a, 32b emits a signal to the corresponding sensor 34a, 34b. The signal from the transmitter can be a light signal, an infra-red signal, a sound signal, a radio signal or the like.

Pressure-sensitive pads 30 are positioned on the top surface of the mattress 4, near the foot or head of the bed.

The purpose of the pressure-sensitive pads 30 is to detect when a bed occupant attempts to get out of the bed. When the detection system switch is turned on, the pressure-sensitive pads 30 detect the weight of the bed occupant and remain stable. Removal of weight from the pressure-sensitive pads 30 is one of the conditions that signal to the control mechanism that the occupant is attempting to get out of the bed. (The control mechanism will be discussed in detail below). When additional conditions are met, the air bag 2 will inflate and an audible alarm will sound. The additional conditions exist when the transmitters 32a, 32b and reflectors/receivers 34a, 34b signals are interrupted.

The pressure sensitive pad in the preferred embodiment includes a rectangular or other suitable shape air-tight bag, made of fabric or a plastic sheet, of suitable size to cover the foot of a patient's bed. The pad should be thin enough when inflated that its presence does not disturb the patient. The preferred thickness of the pad is on the order of an inch. Internal baffles of polyurethane foam or other suitable substance keep the thickness of the pad fixed when the airtight bag is filled with air, rather than allowing the pad to become thicker as it is inflated. A nozzle at a corner of the pad or other suitable location communicates with the inlet of a pressure sensitive switch via a flexible hose of suitable length.

The pressure sensitive switch closes an electrical contact when the air pressure at its inlet port rises above a pre-set and adjustable value. A suitable switch is manufactured by Dwyer Corporation and has a sensitivity range from 0.15 to 0.50 inches of water. When the patient's legs are placed on the pad, the pressure inside rises. The hose communicates this increased pressure to the pressure sensitive switch, which closes its electrical contact. Closing the switch sends a signal to the detection device indicating that the patient's legs have been placed on the pad. When the patient's legs are removed from the pad, the pressure inside drops. This pressure drop is communicated to the pressure sensitive switch, the switch opens and another signal goes to the control mechanism, indicating that the patient's legs are removed from the pad. In use, the pad is placed on the patient's bed under the bed linens. The preferred position of the pad is at the patient's feet near its center in the patient's ordinary sleep position. Then when the feet or legs of the patient are removed from the pad, as in the act of getting out of bed, the switch opens as described above and sends a signal to the detection device.

The pressure-sensitive pads 30 work in conjunction with the transmitters 32a, 32b and reflectors/receivers 34a, 34b to form a detection system. At least one set of transmitters 32a is located side by side and parallel to each other above the head of the bed and is directed toward the foot of the bed. The transmitters emit signals that travel in a substantially horizontal direction relative to and above the bed. In the preferred embodiment the transmitters are positioned at the head of the bed and the reflectors/receivers are positioned at the foot of the bed; however, it is within the scope of this invention that the transmitters and reflectors/receivers can be interchanged between the headboard and the footboard. Each transmitted signal is received by a one or more reflector/receivers 34a located above the foot of the bed, side by side and parallel to each other, facing the head of the bed and aligned with the corresponding transmitters 32a to receive the signal. The transmitters 32a and reflectors/receivers 34a are mounted above the bed on the headboard 22 and footboard 24 of the bed.

In addition, a side transmitter 32b generates signals by the side of or below the side of the bed. This transmitter 32b is paired with corresponding longitudinally spaced reflectors/receivers 34b and located by the side of or below the side of the bed. This side transmitter 32b and reflectors/receivers 34b may be mounted on the vertical legs 20 of the bed frame 10. The side transmitter 32b and reflectors/receivers 34b capture the movement of the bed occupants' arms, legs or feet when they or other body parts of the patient hang over the edge of the bed 10 such as when the occupant attempts to get out of the bed. The side transmitter 32b and reflector/receiver 34b may be affixed to both longitudinal sides of the bed in a plane laterally spaced from and parallel to the support platform 18 or below the platform 18.

In operation, when the detection system is turned on, signals are sent from the transmitters 32a, 32b to the reflectors/receivers 34a, 34b. When the sensor is a receiver, the transmitter 32a, 32b carries a signal and the receiver receives the signal and carries a corresponding signal to the control mechanism indicating receipt of the signal from the transmitter. When the sensor is a reflector, the transmitters 32a, 32b carry the signals and the reflectors 34a, 34b reflect the signal back to the transmitter, which carries a corresponding signal to the control mechanism indicating receipt of the signal from the reflector. When the signals to the control mechanism are interrupted and the occupant attempting to get out of bed removes weight from the pressure sensitive pads, the air bag will inflate.

FIG. 4 illustrates the control mechanism. The control mechanism is attached to the detection system and includes low voltage lines 40 that carry signals to a bed occupancy monitor 42. The bed occupancy monitor, such as the INFORMER manufactured by Micro-Tech Medical, Inc., of West Hartford, Conn., indicates by an alarm or signal when an occupant is attempting to leave the bed. The bed occupancy monitor 42 of the control mechanism receives the signals from the detection system and, in turn, carries a signal to operate an audio system 46 for example, a tape recorder. The audio system 46 produces a recorded voice message simultaneously with the inflating of the air bag that will urge the bed occupant to remain in bed.

Figure 7:
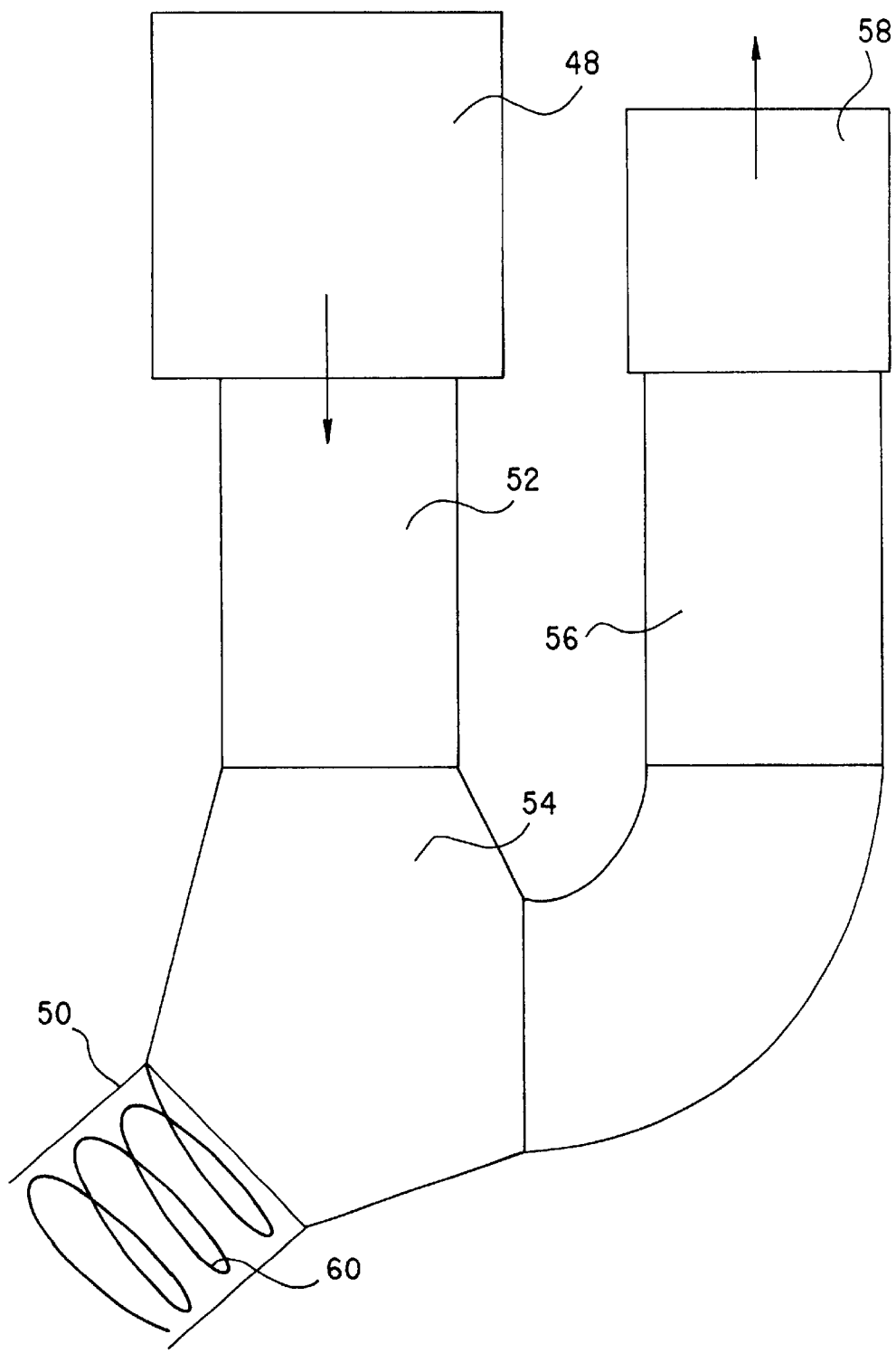
FIG. 7 is a schematic of the inflation/deflation device.

Referring to FIGS. 4, 5 and 7, the air bag 2 is inflated by an inflation device, such as an inflation fan 48 connected through a normally opened valve 52, a manifold 54, and by a flexible duct 50 to the air bag inlet. The inflation fan 48 is activated so that it quickly blows air into the deflated air bag 2 upon a signal from a detection system that the occupant is leaving the bed. The detection system will be discussed in more detail below. The inflated air bag pressure should not exceed ½ psig.

A deflation device in FIG. 7, removes air from the air bag after use. The deflation device includes a normally closed valve 56 and a deflation fan 58. The deflation fan air flow exits the deflation fan opposite the duct 50 so as to draw air out of the air bag. The air bag deflation process is triggered when the audible alarm is canceled by the nurse or caregiver pressing a stop-button (not shown) which may be on the bed occupancy monitor. When the nurse or caregiver presses the stop-button, the normally opened valve 52 closes and the normally closed valve 56 opens. The deflation device removes the air from the air bag through the manifold 54, the normally closed valve 56, and the deflation fan 58 to exit outside of the system. The manifold 54 and flexible duct 50 for the deflation device are the same as those used for the inflation of the air bag. When the air bag is empty, or after a preset time, the deflation fan 58 will stop and both valves 52, 56 will resume their normal positions. The normally closed valve will close and the normally opened valve will re-open. The valves remain in these states of readiness to inflate the air bag when the detection device again detects an occupant attempting to get out of bed.

The inflation fan 48 is preferably located underneath the bed. The tape recorder, and bed occupancy monitor are located in a housing containing the inflation/deflation device and electronics. The tape recorder and bed occupancy monitor are preferably in a separate package. Audio speakers are separate from the control mechanism and are located near the bed for sound clarity.

In operation, when the occupant is in bed, and the power is turned on, the pressure-sensitive pads 30 and the transmitters 32a, 32b and reflectors/receivers 34a, 34b are activated. The activated transmitters 32a, 32b and reflectors/receivers 34a, 34b generate either headboard to footboard or footboard to headboard signals. All of the signals from transmitters to receivers remain constant until interrupted by a body part of the bed occupant. The pads 30, transmitters 32a, 32b and reflectors/receivers 34a, 34b are connected such that the bag will inflate and either an audible alarm will sound, or the voice message will operate, or both when, at least two out of the following three conditions exist at the same time: (1) one of the signals above the bed is interrupted; (2) there is no pressure on the pressure sensitive pads 30; (3) the signal on the side of the bed is interrupted.

The first and second conditions are met when the person sits up in bed, thus interrupting at least one of the signals above the bed, and at the same time moves his or her feet away from the end of the bed. This person has not moved any part of their body off the bed but has sat up and pulled their feet toward their upper body in preparation to do so. The second and third conditions are met when the person moves both feet away from the end of the bed and at the same time puts at least one leg over the side of the bed, interrupting the side signal. This person is lying on the bed with one leg over the side and the other away from the end of the bed, in preparation to put it over the side of the bed as well. The first and third conditions are met when a person sits up in bed and at the same time puts one leg over the side. This person has only one leg over the side of the bed, the other being on the pressure sensitive pads, but is nonetheless preparing to leave the bed. Each of these sets of conditions will cause the audible alarm to sound and the bag to inflate.

The audible alarm will not sound and the voice message will not operate nor will the bag inflate when the occupant puts one leg over the side but retains the other on the pressure-sensitive pads; or when the occupant raises both feet off of the pads, but lies flat in bed; or when the occupant sits up with legs remaining on the pressure sensitive pads.

The audible alarm can be mounted in any suitable position, for example, either on the bed headboard 22 or footboard 24, as well as immediately outside of the patients' room or even at a nursing station. Further, the alarm can be a visual alarm used either alone or in conjunction with the audible alarm. The detection system power switch can be mounted on the bed, nightstand, or on a wall near the bed.

The inflated air bag 2 is suspended above the floor and fixed in an upright position relative to the support frame 12 or the support platform 18 at the headboard 22 and footboard 24 by the support panels 8 as well as tethers 16 made of heavy twine or the like. By being held to the support frame 12 or the support platform 18 at the headboard 22, the air bag 2 remains suspended above the floor and blocks the path of the bed occupant attempting to get out of the bed. The tethers can be bolted or screwed to the support frame 12. Vertical support members 9 are located on the opposite side of the bed from the air bag and anchor the support panels 8.

Sleeves 11 at the ends of the support panels 8 are designed to slip over vertical support members 9. See FIG. 6. Additional suspension of the air bag is accomplished by elastic bands. Elastic bands 14 extend from the support frame 12 at the headboard and footboard of the bed diagonally along the cross-section of the inflated air bag to a point approximately 45 degrees from the edge of the support frame. The elastic bands 14 connect with the tethers 16 at points on the air bag farthest from the support frame 12. The elastic bands can be bolted or screwed to the support frame or vertical support 9.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A method of detecting and deterring bed occupants from getting out of bed including a detection system having transmitters, receivers and pressure sensitive pads for detecting and signaling bed occupant presence; a control mechanism to activate both an audio system and an inflating deterrent for deterring the bed occupant from getting out of bed, comprising the steps of:

detecting that a first signal from a transmitter above the bed is interrupted; and simultaneously detecting that a second signal from a transmitter by a side of the bed is interrupted;

applying a third signal to the audio system, located near the bed, when the first and second signals are detected and operating the audio system in response to the third signal;

producing a voice message, activated by the signal, urging the bed occupant to remain in bed;

triggering the inflation device to inflate the deterrent; and inflating the deterrent.

2. The method according to claim 1, further comprising the step of sounding an audible alarm when at least one signal from a transmitter above the bed is interrupted and when at least one signal from a transmitter by the side of the bed is interrupted.

3. The method according to claim 2, further comprising the step of resetting the detection system and deterrent apparatus including triggering a deflation device to deflate the deterrent and canceling the audible alarm.

4. A method of detecting and deterring bed occupants from getting out of bed including a detection system having transmitters, receivers and pressure sensitive pads for detecting and signaling bed occupant presence; a control mechanism to activate both an audio system and an inflating deterrent for deterring the bed occupant from getting out of bed, comprising the steps of:

detecting that a first signal from a transmitter above the bed is interrupted; and simultaneously detecting an absence of pressure on the pressure sensitive pads;

applying a second signal to the audio system, located near the bed, when the first signal and the absence of pressure are detected and operating the audio system in response to the signal;

producing a voice message, activated by the signal, urging the bed occupant to remain in bed;

triggering the inflation device to inflate the deterrent; and inflating the deterrent.

5. The method according to claim 4, further comprising the step of sounding an audible alarm when at least one signal from a transmitter above the bed is interrupted and when there is no pressure on the pressure sensitive pads.

6. The method according to claim 5, further comprising the step of resetting the detection system and deterrent apparatus including triggering a deflation device to deflate the deterrent and cancel the audible alarm.

7. A method of detecting and deterring bed occupants from getting out of bed including a detection system having transmitters, receivers and pressure sensitive pads for detecting and signaling bed occupant presence; a control mechanism to activate both an audio system and an inflating deterrent for deterring the bed occupant from getting out of bed, comprising the steps of:

detecting that a first signal from a transmitter by a side of the bed is interrupted;

detecting an absence of pressure on the pressure sensitive pads; and applying a second signal to the audio system, located near the bed, when the first signal and the absence of pressure are detected and operating the audio system in response to the signal;

producing a voice message, activated by the signal, urging the bed occupant to remain in bed;

triggering the inflation device to inflate the deterrent; and inflating the deterrent.

8. The method according to claim 7, further comprising the step of sounding an audible alarm when at least one signal from a transmitter beside the bed is interrupted and when there is no pressure on the pressure sensitive pads.

9. The method according to claim 8, further comprising the step of resetting the detection system and deterrent apparatus including triggering a deflation device to deflate the deterrent and cancel the audible alarm.

* * * * *